United States Patent
Caskey et al.

(10) Patent No.: US 6,258,944 B1
(45) Date of Patent: Jul. 10, 2001

(54) OB RECEPTOR ISOFORMS AND NUCLEIC ACIDS ENCODING THEM

(75) Inventors: C. Thomas Caskey, Houston, TX (US); Patricia Hey, Lansdale, PA (US); John W. Hess, Lansdale, PA (US); Michael Sean Phillips, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/827,962

(22) Filed: May 6, 1997

Related U.S. Application Data

(60) Provisional application No. 60/016,899, filed on May 6, 1996.

(51) Int. Cl.[7] ............................ C12N 15/12; C07K 14/72; A61K 38/17; G01N 33/53
(52) U.S. Cl. .................... 536/23.5; 530/350; 435/320.1; 435/325; 435/252.3; 435/252.33; 435/254.11; 435/7.1; 435/7.21; 435/69.1; 514/2
(58) Field of Search ................... 530/350; 514/2; 536/23.5; 435/320.1, 325, 252.3, 252.33, 254.11, 7.1, 7.21, 69.1

(56) References Cited

U.S. PATENT DOCUMENTS 5,643,748    7/1997   Snodgrass et al. .

FOREIGN PATENT DOCUMENTS

| | | |
|---|---|---|
| 2104996 | 1/1994 | (CA) . |
| WO 96/08510 | 3/1996 | (WO) . |
| WO 96/35787 | 11/1996 | (WO) . |
| WO 97/19952 | 6/1997 | (WO) . |
| 97/31015 * | 8/1997 | (WO) . |

OTHER PUBLICATIONS

Considine et al, Diabetes 19, Jul. 1976, p 992–94.*
Phillip et al, Nature Genetics 13, 1996, p18–19.*
Tartaglia, et al. "Identification and Expression Cloning of a Leptin Receptor, OB–R" Cell, vol. 83, pp. 1263–1271, 1995.
Chua, et al. "Phenotypes of Mouse diabetes and Rat fatty Due to Mutations in the OB (Leptin) Receptor" Science, vol. 271, pp. 994–996, 1996.
Chen, et al. "Evidence That the Diabetes Gene Encodes the Leptin Receptor: Identification of a Mutation in the Leptin Receptor Gene in db/db Mice" Cell, vol. 84, pp. 491–495, 1996.
Cioffi, et al. "Novel B219/OB Recptor Isoforms: Possible Role Of Leptin In Hematopoiesis and reproduction "Nature Medicine, vol. 2, No. 5, pp. 585–589, 1996.
Lee, et al. "Abnormal splicing of the leptin receptor in diabetic mice" Nature, vol. 379, pp. 632–635, 1996.
Hodgson, J. "Receptor Screening and the Serach for New Pharmaceuticals" Bio/Technology, vol. 10, pp. 973–997, 1992.
Baumann et al. "The full–length leptin receptor has signalling capabilities of interleukin 6–type cytokine receptors" 1996 Proc. Natl. Acad. Sci. USA 93:8374–8378.
Ghilardi et al. "Defective STAT signaling by the leptin receptor in diabetic mice" 1996 Proc. Natl. Acad. Sci. USA 93:6231–6235.
Guan et al. "Differential expressiion of mRNA for leptin receptor isoforms in the rat brain", 1997 Molec. and Cell. Endocrinology, 133:1–7.
Ilda et al. "Phenotype–linked amino acid alteration in leptin receptor cDNA from zucker fatty (fa/fa) rat" 1996 Biochem. Biophys. Res. Comm. 222:19–26.
Phillips et al. "Leptin receptor missense mutation in the fatty zucker rat", 1996 Nature Genetics 13:18–19.
Rosenblum et al. "Functional STAT 1 and 3 signaling by the leptin receptor (OB–R); reduced expression of the rat fatty leptin receptor in transfected cells," 1996 Endocrinology 137(11):5178–5181.
Spiegelman et al. "Adipogenesis and Obesity: Rounding out the big picture", 1996 Cell 87:377–389.
Stephens et al. "The role of neuropeptide Y in the atiobesity action of the obese gene product", 1995 Nature 277:530–532.
Takaya et al. "Molecular cloning of rat leptin receptor isoform complementary DNAs—identification of a missense mutation in Zucker fatty (fa/fa) rats", 1996 Biochem. Biophys. Res. Comm. 225:75–83.
Wang et al., "A novel leptin receptor isoform in rat", 1996 FEBS Letters 392:87–90.

* cited by examiner

Primary Examiner—David L. Fitzgerald
(74) Attorney, Agent, or Firm—Anna L. Cocuzzo; Joanne M. Giesser

(57) ABSTRACT

The ob receptor has numerous isoforms resulting from alternative splicaing; three novel isoforms, designated c', f, and g are disclosed. The nucleic acids encoding these isoforms are taught. Also part of the invention are vectors containing the nucleic acid encoding the receptors, host cells transformed with these genes, and assays which use the genes or protein isoforms.

28 Claims, No Drawings

OB RECEPTOR ISOFORMS AND NUCLEIC ACIDS ENCODING THEM

CROSS-REFERENCE TO RELATED APPLICATIONS

This application claims priority under 35 U.S.C. § 119(e) to U.S. provisional application serial no. 60/016,899, filed May 6, 1996.

STATEMENT REGARDING FEDERALLY-SPONSORED R&D

Not Applicable

REFERENCE TO MICROFICHE APPENDIX

Not Applicable

FIELD OF THE INVENTION

This invention relates to ob receptor protein isoforms, to DNA and RNA sequences encoding them, and to assays using the receptor isoform proteins.

BACKGROUND OF THE INVENTION

Recently the identification of mutations in several genes involved in the onset of obesity in rodents have been identified. Of particular interest are mutations discovered in the peptide hormone, leptin, which is a component of a novel signal transduction pathway that regulates body weight (Zhang et al. 1994, *Nature* 372:425–432; Chen et al. 1996, *Cell* 84:491–495). Leptin was initially discovered by the positional cloning of the obesity gene, ob, in mice. Two different ob alleles have been identified: one mutation causes the premature termination of the leptin peptide resulting in a truncated protein, and the other mutation changes the transcriptional activity of the obesity (ob) gene, resulting in a reduced amount of circulating leptin.

There is a correlation between a decrease in the levels of biologically active leptin and the overt obese phenotype observed in ob/ob mice. Recombinant leptin has been shown to induce weight loss in the ob/ob mouse but not in the diabetic phenotype db/db mouse (Campfield et al. 1995, *Science* 269: 546–549; Halaas et al. 1995, *Science* 269: 543–546; Pellymounter et al. 1995, Science 269:540–543; Rentsch et al. 1995, *Biochem. Biophys. Res. Comm.* 214:131–136; and Weigle et al. 1995, *J. Clin. Invest.* 96:2065–2070).

Although the synthesis of leptin occurs in the adipocyte, its ability to decrease food intake and increase metabolic rate appears to be mediated centrally by the hypothalamus. Injection of recombinant leptin into the third ventricle of the brain elicits a similar response as peripheral administration of leptin. Furthermore, the recent cloning of the human receptor for the leptin, the ob-receptor (OB-R), reveals that it is transcribed in the hypothalamus (Tartaglia et al. 1995, *Cell* 83:1263–1271; Stephens et al. 1995, *Nature* 377: 530–532). In addition, a mutation that results in premature termination of the long-form of the mouse OB-R, which is preferentially expressed in the hypothalamus, appears to be responsible for the obese phenotype of the db/db mouse (Lee et al. 1996, *Nature* 379:632–635; Chua et al. 1996, *Science* 271:994–996; and Chen et al. 1996, Cell 94:491–495).

The OB-R from wild type (lean) rats and from rats having the fatty mutation (both heterozygous and homozygous fa) have been isolated and sequenced. (patent application Ser. Nos. 60/146,928 and 60/013,969, now 08/803,346, pending filed Feb. 22, 1996 and Mar. 22, 1996, which are hereby incorporated by reference.) The gene encoding the OB-R of the fatty rat bears a missense mutation such that its expression product differs from the wild-type rat OB-R amino acid sequence shown in SEQ ID NO: 15 by the substitution $Gln^{269} \rightarrow Pro$, as shown in SEQ ID NO: 20.

Various isoforms of the OB-Rs have also been identified. These isoforms are due to alternative splicing. For example, in the mouse the a form has 5 amino acids following the Lysine at 889; the b form has 273 amino acids after Lysine 889; the c form has 3 amino acids after Lysine 889; and the d form contains 11 amino acids after Lysine 889.

It would be desirable to be able to further experiment with various isoforms in order to better understand obesity, and to be able to clone and produce novel oh receptor isoforms to use in assays for the identification of ligands which may be useful in understanding obesity and for its prevention and treatment.

SUMMARY OF THE INVENTION

Not Applicable

DETAILED DESCRIPTION OF THE INVENTION

This invention relates to novel ob receptor isoforms designated c', f and g which are substantially free from associated membrane proteins. It also relates to substantially purified ob receptor isoform c', f and g proteins. These isoforms are present in various species, including rat, mouse and human.

Another aspect of this invention is to nucleic acids which encode OB receptor isoforms c', f or g. The nucleic acid may be any nucleic acid which can encode a protein, such as genomic DNA, cDNA, or any of the various forms of RNA. Preferably, the nucleic acid is cDNA.

This invention also includes vectors containing a OB-R isoform c', f or g gene, host cells containing the vectors, and methods of making susbstantially pure OB-R isoform c', f or g protein comprising the steps of introducing a vector comprising a OB-R isoform c', f or g gene into a host cell, and cultivating the host cell under appropriate conditions such that OB-R isoform c', f or g is produced. The OB-R isoform c', f or g so produced may be harvested from the host cells in conventional ways.

Yet another aspect of-this invention are assays which employ OB-R isoform c', f or g. In these assays, various molecules, suspected of being OB-R isoform c', f or g ligands are contacted with a OB-R isoform c', f or g, and their binding is detected. In this way agonists, antagonists, and ligand mimetics may be identified. A further aspect of this invention are the ligands so indentified.

BRIEF DESCRIPTION OF THE SEQUENCES

SEQ ID NO: 1 is the amino acid sequence of residues $Lys^{889}$ through $Asn^{895}$ of the rat OB-R isoform f, corresponding to the alternate exon of that isoform.

SEQ ID NO: 2 is the N-terminal amino acid sequence of the rat OB-R isoform g, corresponding to the alternate exon of that isoform.

SEQ ID NOS: 3, 4, and 7–10 are the sequences of PCR primers, and SEQ ID NOS: 5, 6, and 11–14, respectively, are the amino acid sequence fragments to which they correspond.

SEQ ID NO: 15 shows the amino acid sequence of the wild-type rat OB-R, and SEQ ID NO: 16 provides the corresponding cDNA sequence.

SEQ ID NO: 17 is the sequence of a cDNA encoding the rat OB-R isoform f.

SEQ ID NO: 18 is the sequence of a cDNA encoding the rat OB-R isoform c'.

SEQ ID NO: 19 shows the amino acid sequence of the isoform f protein corresponding to the wild-type rat OB-R.

SEQ ID NO: 20 provides the amino acid sequence of the fatty rat OB-R.

SEQ ID NO: 21 shows the amino acid sequence of the isoform f protein corresponding to the fatty rat OB-R.

As used througout the specification and claims, the following definitions apply:

"Substantially free from associated membrane proteins" means that the receptor protein is not in physical contact with any membrane proteins.

"Substantially purified OB-receptor isoform c', f or g" means that the protein isoform is at least 90% and preferably at least 95% pure.

"Wild type" means that the gene or protein is substantially the same as that found in an animal which is not considered to have a mutation for that gene or protein.

"fa" means that the gene or protein is substantially the same as that found in a rat homologous for the fatty mutation.

"Substantially the same" when referring to a nucleic acid or amino acid sequence means either it is the same as the reference sequence, or if not exactly the same, contains changes which do not affect its biological activity or function.

It has been suprisingly found, in accordance with this invention that the OB-R exists in a large variety of isoforms, including three novel ones, form c', f and g. These isoforms apply to all species, but for convenience, throughout the specification and claims, numberings of amino acids and nucleotides will use the rat wild type sequences (SEQ ID NOS: 15 and 16) as a reference. However, it is to be understood that this invention is not limited to rat wild type proteins and nucleic acids and specifically includes rat (wild type and fatty), mouse, and human OB-R isoform c', f and g proteins and nucleic acids.

OB-R isoform f differs from wild type protein in that after the Lysine at position 889 (referring to the rat sequence in SEQ ID NO: 15 there are six amino acids, ending at an Asparagine residue at position 895. In the cDNA, the codons are then followed by a Stop codon. One cDNA for rat isoform f is shown in SEQ ID NO: 17 this invention specifically includes all various cDNAs encoding an isoform f protein. The superscripted numbers refer to protein position numbers.

$Lys^{889}$ $Iso^{890}$ $Met^{891}$ $Pro^{892}$ $Gly^{893}$ $Arg^{894}$ $Asn^{895}$ (SEQ ID NO: 1)

In the human isoform f, Lysine 891 corresponds to the rat Lysine 889, the same six amino acids follow Lysine 889.

In a particularly preferred embodiment of this invention, the OB-R isoform f is from rat origin.

OB-R isoform g differs from the wild type in that it is much shorter that the wild type sequence. The following eighteen amino acids are found at the beginning of the protein with the superscript numbers indicating their position. The Arginine at position 18 is spliced to a large fragment of the wild type molecule, beginning at the Proline at position 166 (in both mouse and human). This isoform then extends for the remainder of the wild type molecule.

$Met^1$ $Phe^2$ $Gln^3$ $Thr^4$ $Pro^5$ $Arg^6$ $Ile^7$ $Val^8$ $Pro^9$ $Gly^{10}$ $His^{11}Lys^{12}$ $Asp^{13}$ $Leu^{14}Ile15$ $Ser^{16}$ $Lys^{17}$ $Arg^{18}$ $Pro^{166}$... (SEQ ID NO: 2)

After $Pro^{166,}$ the remainder of the protein may be the same as wild type, or, alternatively it could also contain another isoform variation, such as isoform a, b, c, d, e, or f.

A particularly preferred embodiment is the rat isoform g.

OB-R isoform c' is similar to the OB-R isoform c which was previously described [Lee et al., *Nature* 379: 632–635]. After Lysine at position 889, it only has three amino acids, $Val^{890}$ $Thr^{891}$ $Phe^{892}$ Stop. As can be seen, isoform c' differs from isoform c in that the final amino acid is phenylalanine rather than valine found in isoform c. Further, there are untranslated sequences in the DNA encoding isoform c' which do not appear to be present in isoform c. The cDNA encoding the rat isoform c' is given in SEQ ID NO: 18. In humans, the Val, Thr, Phe follow Lysine 891.

One aspect of this invention is the molecular cloning of these various isoforms of OB-R. The wild type and fa receptor proteins contain an extracellular, a transmembrane domain. In the rat, the extracellular domain extends from amino acids 1–830; the transmembrane domain is from amino acids 839–860; and the cytoplasmic domain is from amino acids 860–1162. Similar domains have bene identified for the mouse and human proteins. This invention also includes isoform c', f and g proteins which lack one or more of these domains. Such deleted proteins are useful in assays for identifying ligands and their binding activity.

In the rat wild type protein, amino acids 1–28 form a signal sequence; thus the mature proteins extend from amino acids 28–1162. The mature protein isoforms form yet another aspect of this invention. This differs somewhat from the signal sequence of 1–22 reported for mouse and human OB-R; the mature mouse and human isoforms form yet another aspect of this invention.

The OB-R isoform c', f or g gene can be introduced into virtually any host cell using known vectors. Preferred host cells include *E. coli* as well as mammalian and yeast cell lines.

One of ordinary skill in the art is able to choose a known vector which is appropriate for a given host cell; generally plasmids or viral vectors are preferred. The OB-R isoform c', f or g gene may be present in the vector in its native form, or it may be under the control of a heterologous promoter, and if desired, one or more enhancers, or other sequences known to regulate transcription or translation. The host cell containing the OB-R isoform c', f or g gene is cultured, and the OB-R isoform c', f or g gene is expressed. After a suitable period of time the OB-R c', f or g isoform protein may be harvested from the cell using conventional separation techniques.

A further aspect of this invention is the use of an OB-R c', f or g isoform in assays to identify OB-R c', f or g isoform ligands. A ligand binds to the OB-R isoform receptor, and in vivo may or may not result in an activation of the receptor. Ligands may be agonists of the receptor (i.e. stimulate its activity), antagonists (inhibit its activity) or they may bind with little or no effect upon the receptor activity.

In an assay for ligands, an OB-R isoform of this invention is exposed to a putative ligand, and the amount of binding is measured. The amount of binding may be measured in many ways; for example, a ligand or the OB-R isoform being investigated may be labeled with a conventional label (such as a radioactive or fluorescent label) and then put in contact with the OB-R isoform under binding conditions. After a suitable time, the unbound ligand is separated from the OB-R isoform and the amount of ligand which has bound can be measured. This can be performed with any of the OB-R isoforms of this invention; alternatively the amount of binding of the various isoforms can be compared. In a competitive assay, both the putative ligand and a known ligand are present, and the amount of binding of the putative ligand is compared to the amount of binding to a known ligand. Alternatively, the putative ligand's ability to displace previously bound known ligand (or vice-versa) may be measured. In yet other embodiments, the assay may be a heterogeneous one, where the OB-R isoform may be bound to a surface, and contacted with putative ligands. Dectection of binding may be by a variety of methods, including labelling, reaction with antibodies, and chomophores.

In another assay, the OB-R isoforms of this invention may be used in a "trans" activation assay. Such assays are described in U.S. application Ser. No. 60/016,051, now U.S. Pat. No. 6,007,998, which was filed on Apr. 22, 1996 and which is hereby incorporated by reference. In this assay, a cell which expresses an OB-R isoform of this invention (either naturally or through recombinant means) is transfected with a reporter gene construct comprising a minimal promoter, a leptin activation element and a reporter gene. Transcription of the reporter gene is dependant upon activation of the leptin activation element. Binding of a ligand to the receptor isoform activates the leptin activation element, which then allows transcription of the reporter gene.

The following non-limiiting Examples are presented to better illustrate the invention.

EXAMPLE 1

Preparation of mRNA and cDNA from Rat Tissues

Tissues were collected from lean and falfa Zucker rats and snap frozen in liquid nitrogen. The tissues collected included: hypothalamus, pituitary, lung, liver, kidney, heart, adrenal glands, smooth muscle, skeletal muscle, and adipose tissue. The tissues were homogenized with a Brinkmann Polytron homogenizer in the presence of guanadinium isothiocyanate. mRNA was prepared from hypothalamus, lung, and kidney according to the instructions provided with the messenger RNA isolation kit (Stratagene, La Jolla, Calif.). cDNA was prepared from approximately 2 $\mu$g of mRNA with the Superscript™ choice system (Gibco/BRL Gaithersburg, Md.). The first strand cDNA synthesis was primed using 1 $\mu$g of oligo(dT) 12–18 primer and 25 ng of random hexamers per reaction. Second strand cDNA sythesis was performed according to the manufacturer's instructions. The quality of the cDNA was assessed by labeling an aliqout ($\frac{1}{10}^{th}$) of the second strand reaction with approximately 1 $\mu$Ci of [$\alpha$-$^{32}$P]dCTP (3000 Ci/mmol). The labeled products were separated on an agarose gel and detected by autoradiography.

EXAMPLE 2

Preparation of a Hypothalamic cDNA Library

Approximately 3.6 $\mu$g of phosphorylatedBstXI adapters (Invitrogen, San Diego, Calif. ) were ligated to approximately 3 $\mu$g of cDNA prepared as described in Example 1. The ligation mix was then diluted and size-fractionated on a cDNA sizing column (Gibco/BRL Gaithersburg, Md.). Drops from the column were collected and the eluted volume from the column was determined. An aliqout from each fraction was analyzed on an agarose gel. Fractions containing cDNA of greater than or equal to 1 kb were pooled and precipitated.

The size-fractionated cDNA with the Bst XI adapters was ligated into the prokaryotic vector pcDNA II (Invitrogen, San Diego, Calif.). The vector (4 $\mu$g) was prepared for ligation by first cutting with the restriction endonuclease Bst XI, gel purifying the linearized vector, and then dephosphorylating the ends with calf intestinal phosphatase (Gibco/BRL, Gaithersburg, Md.) according to the manufacturers instructions. The ligation contained approximately 10–20 ng of cDNA and approximately 100 ng of vector and was incubated overnight at 14° C. The ligation was transformned into 1 ml of XL-2 Blue Ultracompetent cells (Stratagene, La Jolla, Calif.) according to the manufacture's intructions. The transfoilned cells were spread on 133 mm Colony/Plaque Screen filters (Dupont/NEN, Boston, Mass.), plated at a density of 30,000 to 60,000 colonies per plate on Luria Broth agar plates containing 100 $\mu$g/ml Ampicillin (Sigma, St. L ouis, Mo.).

EXAMPLE 3

Screening a Hypothalamic cDNA Library

Colonies on filters were replica plated onto a second filter set. The master filter was stored at 4° C. for subsequent isolation of regions containing colonies that gave a positive hybridization signal. The replica filters were grown for several hours at 37° C. until colonies were visible and then processed for in situ hybridization of colonies according to established procedures (Maniatis, et al. *Molecular Cloning: A Laboratory Manual,* Cold Spring Harbor Laboratory Publications, Cold Spring Harbor, N.Y., which is hereby incorporated by reference). A Stratalinker (Stratagene, La Jolla, Calif.) was used to crosslink the DNA to the filter. The filters were washed at 55° C. for 2 hours in 2× SSC and 0.5% SDS to remove bacterial debris. Eight to ten filters were then placed in a heat sealable bag (Kapak, Minneapolis, Minn.) containing 15–20 ml of 1× hybridization solution (Gibco/BRL, Gaithersburg, Md.) containing 50% foimnamide and incubated for 1 hour at 42° C. The filters were hybridized overnight with greater than 1,000,000 cpm/ml of the radiolabeled probe described below in 1× hybridization buffer (Gibco/BRL, Gaithersburg, Md.) containing 50% formamide at 42° C. The probe, a 2.2 kb fragment encoding the extracellular portion of the Ob-R was labeled by random priming with [alpha $^{32}$P]dCTP (3000 Ci/mmole, Amersham, Arlington Heights, Ill.) using redi-prime (Amersham, Arlington Heights, Ill.). The probe was purified from unincorporated nucleotides using a Probequant G-50 spin column (Pharmacia Biotech, Piscataway, N.J.). Filters were washed two times with 0.1× SSC 0.1 % SDS at 60° C. for 30 min and then subjected to autoradiography. Individual regions containing hybridization positive colonies were lined up with the autoradiogram of the hybridized filter. These were excised from the master filter, and placed into 0.5 ml Luria broth plus 20% glycerol. Each positive was replated at a density of approximate 50–200 colonies per 100 by 15 mm plate and screened by hybridization as previously described. Individual positive colonies were picked and plasmid DNA was prepared from an overnight culture using a Wizard kit (Promega, Madison, Wis.).

EXAMPLE 4

Amplification of Lean Rat OB-receptor cDNA Using PCR

To provide for a probe to screen the hypothalamic cDNA library, the rat OB receptor was initially obtained by PCR using degenerate primers based on the mouse and human OB-receptor amino acid sequences. A set of oligonucleotide primers, were designed to regions with low codon degeneracy. The pairing of the forward primers ROBR 2 (5'-CAY TGG GAR TTY CTI TAY GT-3'SEQ ID NO: 3) and ROBR 3 (5'-GAR TGY TGG ATG AAY GG-3'SEQ ID NO: 4) corresponding to mouse amino acid sequences HWEFLYV (SEQ ID NO: 5) and ECWMKG(SEQ ID NO: 6), with reverse primers ROBR 6 (5 '-ATC CAC ATI GTR TAI CC-3'SEQ ID NO: 7), ROBR 7 (5'-CTC CAR TTR CTC CAR TAI CC-3'SEQ ID NO: 8), ROBR 8 (5'-ACY TTR CTC ATI GGC CA-3'SEQ ID NO: 9) and ROBR 9 (5'-CCA YTT CAT ICC RTC RTC-3'SEQ ID NO: 10) representing mouse amino acids, GYTMWI(SEQ ID NO: 11), VYWSNWS(SEQ ID NO: 12), WPMSKV(SEQ ID NO: 13), and DDGMKW (SEQ ID NO: 14) provided good yields of the appropriately sized products. The fragments of interest were amplified as long polymerase chain reaction (PCR) products by a modifying the method of Barnes (1994, *Proc. Natl. Acad. Sci.* 91:2216–2220, which is hereby incorporated by reference). In order to obtain the required long PCR fragments, Taq Extender (Stratagene, La Jolla Calif.) and the Expand Long Template PCR System (Boehringer Mannheim, Indianapolis, Ind) were used in combination. The standard PCR reaction mix, in a final volume of 20 μl, contained 5 ng of template (lean rat cDNA), 100 ng of primers, 500 μM dNTPs, 1 X Buffer 3 from the Expand kit, 0.1 μl each of Taq Polymerase and Taq Expander. Reactants were assembled in thin walled reaction tubes. The amplification protocol was: 1 cycle of 92° C. for 30 sec., followed by 32 cycles at 92° C. for 30 sec., 45° C. for 1 min. and 68° C. for 3 min. using a Perkin-Elmer (Norwalk, CT) 9600 Thermal Cycler.

This strategy produced a series of PCR products with the largest being approximately 2.2 Kbp amplified from primers ROBR 2 and ROBR 9. These products were subcloned for DNA sequence analysis as described below. The insert was excised from the cloning vector with the restriction endonuclease Eco RI, and fragments were separated from the vector by agarose gel electrophoresis. The fragments were eluted from the gel using a Prep-A-Gene kit (BioRad, Richmond Calif.) according to the manufacturer's instructions and radiolabeled as described above.

EXAMPLE 5

Subcloning of PCR Products

PCR products of the appropriate size were prepared for subcloning by separation on an agarose gel, excising the band, and extracting the DNA using Prep-A-Gene (BioRad, Richmond, Calif.). PCR products were ligated into pCR™II (Invitrogen, San Diego, Calif.) according to the instructions provided by the manufacturer. The ligation was transformed into INVaF' cells and plated on Luria-Bertani plates containing 100 μg/ml ampicillin and X-Gal (32 μl of 50 mg/ml X-Gal (Promega, Madison, Wis.). White colonies were picked and grown overnight in Luria-Bertani broth plus 100 μg/ml ampicillin. Plasmid DNAs were prepared using the Wizard miniprep kit (Promega, Madison, Wis.). Inserts were analyzed by digesting the plasmid DNA with EcoRI and separating the restriction endonulease digestion products on an agarose gel.

Plasmid DNA was prepared for DNA sequencing by ethanol precipitation of Wizard miniprep plasmid DNA and resuspending in water to achieve a final DNA concentration of 100 μg/ml. DNA sequence analysis was performed using the ABI PRISM™ dye terminator cycle sequencing ready reaction kit with AmpliTaq DNA polymerase, FS. The initial DNA sequence analysis was performed with M13 forward and reverse primers, subsequently primers based on the rat OB-R sequence were utilized. Following amplification in a Perkin-Elmer 9600, the extension products were purified and analyzed on an ABI PRISM 377 automated sequencer (Perkin Elmer, Norwalk, Conn.). DNA sequence data was analyzed with the Sequencher program.

What is claimed is:

1. An Ob-receptor (OB-R) isoform f polypeptide substantially free from associated proteins,
   wherein the amino acid sequence of the isoform f polypeptide corresoonds to the sequence of a native mammalian OB-R from the N-terminus of the polypeptide up to and including the residue corresponding to Lys$^{889}$ of the wild-type rat OB-R,
   and wherein the sequence of the polypeptide further has the C-terminal sequence Ile-Met-Pro-Gly-Arg-Asn (residues 2–7 of SEQ ID NO: 1) immediately following said residue corresponding to Lys$^{889}$ of the wild-type rat OB-R.

2. An OB-R isoform according to claim 1 which is substantially pure.

3. An OB-R isoform f polypeptide according to claim 1, wherein the native mammalian OB-R is a rat OB-R.

4. An OB-R isoform f polypeptide according to claim 3, wherein the rat OB-R is a wild-type rat OB-R.

5. An OB-R isoform f polypeptide according to claim 4, having the amino acid sequence shown in SEQ ID NO: 19.

6. An OB-R isoform f polypeptide according to claim 3, wherein the rat OB-R is a fatty rat OB-R.

7. An OB-R isoform f polypeptide according to claim 6, having the amino acid sequence shown in SEQ ID NO: 21.

8. An OB-R isoform f polypeptide according to claim 1, wherein the native mammalian OB-R is a wild-type murine OB-R.

9. An OB-R isoform f polypeptide according to claim 1, wherein the native mammalian OB-R is a wild-type human OB-R.

10. An isolated nucleic acid molecule comprising a contiguous nucleotide sequence encoding an OB-R isoform f polypeptide according to claim 1.

11. An isolated nucleic acid molecule comprising a contiguous nucleotide sequence encoding an OB-R isoform f polypeptide according to claim 3.

12. An isolated nucleic acid molecule comprising a contiguous mucleotide sequence encoding an OB-R isoform f polypeplide according to claim 5.

13. A nucleic acid molecule according to claim 12, comprising the nucleotide sequence shown in SEQ ID NO: 17.

14. A vector comprising the sequence of a nucleic acid molecule according to claim 10.

15. A vector according to claim 14, wherein the vector is a plasmid.

16. A host cell comprising a vector according to claim 14.

17. A host cell according to claim 16, wherein the host cell is an *E. coli* cell, a mammalian cell, or a yeast cell.

18. A host cell according to claim 17, wherein the amino acid sequence of the OB-R isoform f polypeptide encoded by the sequence in the vector corresponds to the sequence of a native wild-type rat OB-R from its N-terminus up to and including the residue corresponding to $Lys^{889}$.

19. A host cell according to claim 18, wherein the OB-R isoform f polypeptide has the amino acid sequence shown in SEQ ID NO: 19.

20. A host cell according to claim 19, wherein the vector comprises the nucleotide sequence shown in SEQ ID NO: 17.

21. An assay to determine whether a putative ligand binds to OB-R isoform f, comprising:

contacting the putative ligand with an OB-R isoform f polypeptide according to claim 1, and detecting any binding of the putative ligand to the polypeptide.

22. An assay according to claim 21, wherein the putative ligand is labeled.

23. An assay to determine whether a putative ligand binds to OB-R isoform f, comprising:

contacting the putative ligand with an OB-R isoform f polypeptide according to claim 3, and detecting any binding of the putative ligand to the polypeptide.

24. An assay to determine whether a putative ligand bids to OB-R isoform f, comprising:

contacting the putative ligand with an OB-R isoform f polypeptide according to claim 5, and detecting any binding of the putative ligand to the polypeptide.

25. An assay to determine whether a putative ligand binds to OB-R isoform f, comprising:

contacting the putative ligand with a cell according to claim 16, wherein the cell expresses the encoded OB-R isoform f polypeptide, and detecting any binding of the putative ligand to the polypeptide.

26. An assay according to claim 25, wherein the putative ligand is labeled.

27. An assay to determine whether a putative ligand binds to OB-R isoform f, comprising:

contacting the putative ligand with a cell according to claim 18, wherein the cell expresses the encoded OB-R isoform f polypeptide, and detecting any binding of the putative ligand to the polypeptide.

28. An assay to determine whether a putative ligand binds to OB-R isoform f, comprising:

contacting the putative ligand with a cell according to claim 19, wherein the cell expresses the encoded OB-R isoform f polypeptide, and detecting any binding of the putative ligand to the polypeptide.

* * * * *

SEQUENCE LISTING

```
<160> NUMBER OF SEQ ID NOS:  21

<210> SEQ ID NO 1
<211> LENGTH: 7
<212> TYPE: PRT
<213> ORGANISM: Rattus Norvegicus

<400> SEQUENCE: 1

Lys Ile Met Pro Gly Arg Asn
  1               5

<210> SEQ ID NO 2
<211> LENGTH: 19
<212> TYPE: PRT
<213> ORGANISM: Rattus Norvegicus

<400> SEQUENCE: 2
```

```
Met Phe Gln Thr Pro Arg Ile Val Pro Gly His Lys Asp Leu Ile Ser
 1               5                  10                  15

Lys Arg Pro

<210> SEQ ID NO 3
<211> LENGTH: 20
<212> TYPE: DNA
<213> ORGANISM: Artificial Sequence
<220> FEATURE:
<223> OTHER INFORMATION: n= a or g or c or t
      PCR Primer

<400> SEQUENCE: 3
caytgggart tyctntaygt                                              20

<210> SEQ ID NO 4
<211> LENGTH: 17
<212> TYPE: DNA
<213> ORGANISM: Artificial Sequence
<220> FEATURE:
<223> OTHER INFORMATION: PCR Primer

<400> SEQUENCE: 4
gartgytgga tgaaygg                                                 17

<210> SEQ ID NO 5
<211> LENGTH: 7
<212> TYPE: PRT
<213> ORGANISM: Mus Musculus

<400> SEQUENCE: 5

His Trp Glu Phe Leu Tyr Val
 1               5

<210> SEQ ID NO 6
<211> LENGTH: 6
<212> TYPE: PRT
<213> ORGANISM: Mus Musculus

<400> SEQUENCE: 6

Glu Cys Trp Met Lys Gly
 1               5

<210> SEQ ID NO 7
<211> LENGTH: 17
<212> TYPE: DNA
<213> ORGANISM: Artificial Sequence
<220> FEATURE:
<223> OTHER INFORMATION: n= a or g or c or t
      PCR Primer

<400> SEQUENCE: 7
atccacatng trtancc                                                 17

<210> SEQ ID NO 8
<211> LENGTH: 20
<212> TYPE: DNA
<213> ORGANISM: Artificial Sequence
<220> FEATURE:
<223> OTHER INFORMATION: n= a or g or c or t
      PCR Primer

<400> SEQUENCE: 8
ctccarttrc tccartancc                                              20
```

```
<210> SEQ ID NO 9
<211> LENGTH: 17
<212> TYPE: DNA
<213> ORGANISM: Artificial Sequence
<220> FEATURE:
<223> OTHER INFORMATION: n= a or g or c or t
      PCR Primer

<400> SEQUENCE: 9
acyttrctca tnggcca                                                17

<210> SEQ ID NO 10
<211> LENGTH: 18
<212> TYPE: DNA
<213> ORGANISM: Artificial Sequence
<220> FEATURE:
<223> OTHER INFORMATION: n= a or g or c or t
      PCR Primer

<400> SEQUENCE: 10
ccayttcatn ccrtcrtc                                               18

<210> SEQ ID NO 11
<211> LENGTH: 6
<212> TYPE: PRT
<213> ORGANISM: Mus Musculus

<400> SEQUENCE: 11

Gly Tyr Thr Met Trp Ile
1               5

<210> SEQ ID NO 12
<211> LENGTH: 7
<212> TYPE: PRT
<213> ORGANISM: Mus Musculus

<400> SEQUENCE: 12

Val Tyr Trp Ser Asn Trp Ser
1               5

<210> SEQ ID NO 13
<211> LENGTH: 6
<212> TYPE: PRT
<213> ORGANISM: Mus Musculus

<400> SEQUENCE: 13

Trp Pro Met Ser Lys Val
1               5

<210> SEQ ID NO 14
<211> LENGTH: 6
<212> TYPE: PRT
<213> ORGANISM: Mus Musculus

<400> SEQUENCE: 14

Asp Asp Gly Met Lys Trp
1               5

<210> SEQ ID NO 15
<211> LENGTH: 1162
<212> TYPE: PRT
<213> ORGANISM: Rattus Norvegicus

<400> SEQUENCE: 15

Met Thr Cys Gln Lys Phe Tyr Val Val Leu Leu His Trp Glu Phe Leu
1               5                   10                  15
```

-continued

```
Tyr Val Ile Thr Ala Leu Asn Leu Ala Tyr Pro Thr Ser Pro Trp Arg
            20                  25              30
Phe Lys Leu Phe Cys Ala Pro Pro Ser Thr Thr Asp Asp Ser Phe Leu
            35                  40              45
Ser Pro Ala Gly Val Pro Asn Asn Thr Ser Ser Leu Lys Gly Ala Ser
 50                  55                  60
Glu Ala Leu Val Glu Ala Lys Phe Asn Ser Thr Gly Ile Tyr Val Ser
 65                  70                  75                  80
Glu Leu Ser Lys Thr Ile Phe His Cys Cys Phe Gly Asn Glu Gln Gly
                85                  90                  95
Gln Asn Cys Ser Ala Leu Thr Gly Asn Thr Glu Gly Lys Thr Leu Ala
            100                 105                 110
Ser Val Val Lys Pro Leu Val Phe Arg Gln Leu Gly Val Asn Trp Asp
            115                 120                 125
Ile Glu Cys Trp Met Lys Gly Asp Leu Thr Leu Phe Ile Cys His Met
            130                 135                 140
Glu Pro Leu Leu Lys Asn Pro Phe Lys Asn Tyr Asp Ser Lys Val His
145                 150                 155                 160
Leu Leu Tyr Asp Leu Pro Glu Val Ile Asp Asp Leu Pro Leu Pro Pro
                165                 170                 175
Leu Lys Asp Ser Phe Gln Thr Val Gln Cys Asn Cys Ser Val Arg Glu
                180                 185                 190
Cys Glu Cys His Val Pro Val Pro Arg Ala Lys Val Asn Tyr Ala Leu
                195                 200                 205
Leu Met Tyr Leu Glu Ile Thr Ser Ala Gly Val Ser Phe Gln Ser Pro
210                 215                 220
Leu Met Ser Leu Gln Pro Met Leu Val Val Lys Pro Asp Pro Pro Leu
225                 230                 235                 240
Gly Leu Arg Met Glu Val Thr Asp Asp Gly Asn Leu Lys Ile Ser Trp
                245                 250                 255
Asp Ser Gln Thr Lys Ala Pro Phe Pro Leu Gln Tyr Gln Val Lys Tyr
                260                 265                 270
Leu Glu Asn Ser Thr Ile Val Arg Glu Ala Ala Glu Ile Val Ser Asp
            275                 280                 285
Thr Ser Leu Leu Val Asn Ser Val Leu Pro Gly Ser Ser Tyr Glu Val
290                 295                 300
Gln Val Arg Ser Lys Arg Leu Asp Gly Ser Gly Val Trp Ser Asp Trp
305                 310                 315                 320
Ser Leu Pro Gln Leu Phe Thr Thr Gln Asp Val Met Tyr Phe Pro Pro
                325                 330                 335
Lys Ile Leu Thr Ser Val Gly Ser Asn Ala Ser Phe Cys Cys Ile Tyr
                340                 345                 350
Lys Asn Glu Asn Gln Thr Ile Ser Ser Lys Gln Ile Val Trp Trp Met
            355                 360                 365
Asn Leu Ala Glu Lys Ile Pro Glu Thr Gln Tyr Asn Thr Val Ser Asp
            370                 375                 380
His Ile Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
            420                 425                 430
```

```
Ser Cys Glu Thr Asp Gly Tyr Leu Thr Lys Met Thr Cys Arg Trp Ser
            435                 440                 445

Pro Ser Thr Ile Gln Ser Leu Val Gly Ser Thr Val Gln Leu Lys Tyr
        450                 455                 460

His Arg Arg Ser Leu Tyr Cys Pro Asp Asn Pro Ser Ile Arg Pro Thr
465                     470                 475                 480

Ser Glu Leu Lys Asn Cys Val Leu Gln Thr Asp Gly Phe Tyr Glu Cys
                485                 490                     495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
            515                 520                 525

Pro Asp Ser Val Val Lys Pro Leu Pro Pro Ser Asn Val Lys Ala Glu
        530                 535                 540

Ile Thr Ile Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Asn Gly
                565                 570                 575

Lys Glu Ile Gln Trp Lys Thr His Glu Val Phe Asp Ala Lys Ser Lys
            580                 585                 590

Ser Ala Ser Leu Pro Val Ser Asp Leu Cys Ala Val Tyr Val Val Gln
        595                 600                 605

Val Arg Cys Arg Arg Leu Asp Gly Leu Gly Tyr Trp Ser Asn Trp Ser
        610                 615                 620

Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
                645                 650                 655

Asn Val Thr Leu Leu Trp Lys Pro Leu Met Lys Asn Asp Ser Leu Cys
                660                 665                 670

Ser Val Arg Arg Tyr Val Val Lys His Arg Thr Ala His Asn Gly Thr
        675                 680                 685

Trp Ser Gln Asp Val Gly Asn Gln Thr Asn Leu Thr Phe Leu Trp Ala
        690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
                725                 730                 735

Asn Ala Val Gln Ser Leu Ser Ala Tyr Pro Leu Ser Ser Ser Cys Val
            740                 745                 750

Ile Leu Ser Trp Thr Leu Ser Pro Asn Asp Tyr Ser Leu Leu Tyr Leu
        755                 760                 765

Val Ile Glu Trp Lys Asn Leu Asn Asp Asp Gly Met Lys Trp Leu
        770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
            805                 810                 815

Val Gly Lys Pro Lys Ile Ile Asn Gly Phe Thr Lys Asp Asp Ile Ala
            820                 825                 830

Lys Gln Gln Asn Asp Ala Gly Leu Tyr Val Ile Val Pro Ile Ile Ile
            835                 840                 845
```

```
Ser Ser Cys Val Leu Leu Leu Gly Thr Leu Leu Ile Ser His Gln Arg
    850                 855                 860

Met Lys Lys Leu Phe Trp Asp Val Pro Asn Pro Lys Asn Cys Ser
865                 870                 875                 880

Trp Ala Gln Gly Leu Asn Phe Gln Lys Pro Glu Thr Phe Glu His Leu
                885                 890                 895

Phe Thr Lys His Ala Glu Ser Val Ile Phe Gly Pro Leu Leu Leu Glu
                900                 905                 910

Pro Glu Pro Val Ser Glu Glu Ile Ser Val Asp Thr Ala Trp Lys Asn
                915                 920                 925

Lys Asp Glu Met Val Pro Ala Ala Met Val Ser Leu Leu Leu Thr Thr
        930                 935                 940

Pro Asp Ser Thr Arg Gly Ser Ile Cys Ile Ser Asp Gln Cys Asn Ser
945                 950                 955                 960

Ala Asn Phe Ser Gly Ala Gln Ser Thr Gln Gly Thr Cys Glu Asp Glu
                965                 970                 975

Cys Gln Ser Gln Pro Ser Val Lys Tyr Ala Thr Leu Val Ser Asn Val
                980                 985                 990

Lys Thr Val Glu Thr Asp Glu Glu Gln Gly Ala Ile His Ser Ser Val
        995                 1000                1005

Ser Gln Cys Ile Ala Arg Lys His Ser Pro Leu Arg Gln Ser Phe Ser
    1010                1015                1020

Ser Asn Ser Trp Glu Ile Glu Ala Gln Ala Phe Phe Leu Leu Ser Asp
1025                1030                1035                1040

His Pro Pro Asn Val Ile Ser Pro Gln Leu Ser Phe Ser Gly Leu Asp
                1045                1050                1055

Glu Leu Leu Glu Leu Glu Gly Asn Phe Pro Glu Glu Asn His Gly Glu
                1060                1065                1070

Lys Ser Val Tyr Tyr Leu Gly Val Ser Ser Gly Asn Lys Arg Glu Asn
                1075                1080                1085

Asp Met Leu Leu Thr Asp Glu Ala Gly Val Leu Cys Pro Phe Pro Ala
                1090                1095                1100

His Cys Leu Phe Ser Asp Ile Arg Ile Leu Gln Glu Ser Cys Ser His
1105                1110                1115                1120

Phe Val Glu Asn Asn Leu Asn Leu Gly Thr Ser Gly Lys Asn Phe Val
                1125                1130                1135

Pro Tyr Met Pro Gln Phe Gln Ser Cys Ser Thr His Ser His Lys Ile
                1140                1145                1150

Ile Glu Asn Lys Met Cys Asp Leu Thr Val
        1155                1160

<210> SEQ ID NO 16
<211> LENGTH: 3650
<212> TYPE: DNA
<213> ORGANISM: Rattus Norvegicus

<400> SEQUENCE: 16 tgggcaatt  gggctgacct  ttcttatgct  gggatgtgcc  ttggaggact  atgggtgtct      60
atctctgaag  taagatgacg  tgtcagaaat  tctatgtggt  tttgttacac  tgggaatttc    120
tgtatgtgat  aactgcactt  aacctggcct  atccaacctc  tccctggaga  tttaagctgt    180
tttgtgcgcc  accgagtaca  actgatgact  cctttctctc  tcctgctgga  gtcccaaaca    240
atacttcgtc  tttgaagggg  gcttctgaag  cacttgttga  agctaaattt  aattcaactg    300
gtatctacgt  ttctgagtta  tccaaaacca  ttttccactg  ttgctttggg  aatgagcaag    360
```

-continued

```
gtcaaaactg ctccgcactc acaggcaaca ctgaagggaa gacgctggct tcagtggtga    420
agcctttagt tttccgccaa ctaggtgtaa actgggacat agagtgctgg atgaaagggg    480
acttgacatt attcatctgt catatggaac cattacttaa gaaccccttc aagaattatg    540
actctaaggt tcaccttta tatgatctgc ctgaagttat agatgatttg cctctgcccc    600
cactgaaaga cagcttcag actgtccagt gcaactgcag tgttcgggaa tgcgaatgtc     660
atgtaccagt acccagagcc aaagtcaact acgctcttct gatgtattta gaaatcacat    720
ctgctggtgt gagtttcag tcacctctaa tgtcactgca gcccatgctt gttgtgaagc     780
ccgatccacc gctgggtttg cgtatggaag tcacagatga tggtaattta aagatttcat    840
gggacagcca aacaaaagca ccatttccac ttcaatatca ggtgaaatat ttagagaatt    900
ctacaatcgt aagagaggct gctgaaatcg tctcggatac atctctgctg gtaaacagcg    960
tgcttcctgg gtcttcatac gaggtccagg tgaggagcaa gagactggat ggctcaggag    1020
tctggagtga ctggagttta cctcaactct ttaccacaca agatgtcatg tattttccac    1080
ccaaaattct gacgagtgtt ggatccaatg cttccttttg ctgcatctac aaaaatgaga    1140
accagactat ctcctcaaaa caaatagttt ggtggatgaa tctagccgag aagatccccg    1200
agacacagta caacactgtg agtgaccaca ttagcaaagt cactttctcc aacctgaaa    1260 ccaccagacc tcgagggaag tttacctatg atgcagtgta ctgctgcaat gagcaggct    1320 gccatcaccg ctacgctgaa ttatatgtga tcgatgtcaa tatcaatata tcatgtgaa    1380 ctgacgggta cttaactaaa atgacttgca gatggtcacc cagcacaatc caatcatag    1440 tgggaagcac tgtgcagttg aagtatcaca ggcgcagcct gtactgtccc gataaccat    1500 ctattcgtcc tacatcagag ctcaaaaact gcgtcttaca gacagatggc ttttgaat    1560 gtgttttcca gccaatcttt ctattatctg gctatacaat gtggatcagg atcaccatt    1620 ctttaggttc acttgactct ccaccaacgt gtgtccttcc tgactccgta gtaaaccac    1680 tacctccatc taatgtaaaa gcagagatta ctataaacac tggattattg aagtatctt    1740 gggaaaagcc agtctttcca gagaataacc ttcagttcca gattcgatat gcttaaatg    1800 gaaaagaaat acaatggaag acacacgagg tattcgatgc aaaatcaaaatcggccagcc    1860 tgccagtgtc agatctctgt gcggtctatg tggtacaggt tcgctgccg cggttggatg    1920 gactagggta ttggagtaat tggagcagtc cagcctacac tcttgtcag gatgtaaaag    1980 ttcctatgag agggcctgaa ttctggagaa taatggatgg ggatattct aaaaggaga    2040 gaaatgtcac cttgctttgg aagccactga tgaaaaatga ctcacttgt agtgtgagga    2100 ggtatgtggt gaagcatcgt actgcccaca atgggacatg tcacagat gtgggaaatc     2160 agaccaatct cactttcctg tgggcagaat cagcacacac tgttcagtt ctggccatca    2220 attccatcgg tgcctcccctt gtgaatttta accttacgtt ctctggccc atgagtaaag    2280 tgaatgctgt gcagtcactc agtgcttatc ccctgagcag cactgcgtc atcctttcct    2340 ggacactgtc acctaatgat tatagtctgt tatatctggt tttgaatgg aagaaccta    2400 atgatgatga tggaatgaag tggcttagaa tcccttcgaa gttaacaag tattatatcc    2460 atgataattt tattcctatc gagaaatatc agtttagtctttacccagta tttatggaag    2520 gagttggaaa accaaagata attaatggtt tcaccaaag tgatatcgcc aaacagcaaa    2580
atgatgcagg gctgtatgtc attgtaccga taattattc ctcttgtgtc ctgctgctcg    2640
gaacactgtt aatttcacac cagagaatga aaaagttttt ttgggacgat gttccaaacc    2700
```

-continued

```
ccaagaattg ttcctgggca caaggactta atttccaaa gcctgaaaca tttgagcatc    2760 ttttttaccaa gcatgcagaa tcagtgatat ttggtctct tcttctggag cctgaaccag   2820
tttcagaaga aatcagtgtc gatacagctt ggaaaataa agatgagatg gtaccagcag    2880
ctatggtctc acttcttttg accactccag attcacaag gggttctatt tgtatcagtg    2940
accagtgtaa cagtgctaac ttctctgggg ctagagcac caagggaacc tgtgaggatg    3000
agtgtcagag tcaaccctca gttaaatatg cacgctggt cagcaacgtg aaaacagtgg    3060
aaactgatga agagcaaggg gctatacata ttctgtcag ccagtgcatc gccaggaaac    3120 attcccact gagacagtct ttttctagcaactcctggga gatagaggcc caggcatttt     3180 tcctttatc agatcatcca cccaatgtg tttcaccaca actttcattc tcagggttgg     3240
atgagctttt ggaactggag ggaaatttc ctgaagaaaa tcacggggaa aaatctgtgt    3300
attatctagg agtctcctca ggaaacaaa gagagaatga tatgcttttg actgatgagg    3360 cagggtatt gtgcccattc ccagctact gtctgttcag tgacatcaga atcctccagg     3420
agagttgttc acactttgta gaaaaaatt tgaatttagg gacctctggt aagaactttg    3480
taccttacat gccccagttt caatctgtt ccactcacag tcataagata atagaaaata    3540
agatgtgtga cttaactgtg taacttgtc caaaaacttc caggttccat tccagtagag    3600
tgtgtcatgt ataatatgtt ctttatagt tgtgggtggg agagaaagcc              3650
```

<210> SEQ ID NO 17
<211> LENGTH: 3495
<212> TYPE: DNA
<213> ORGANISM: Rattus Norvegicus

<400> SEQUENCE: 17

```
tggggcaatt gggctgacct ttcttatgct gggatgtgcc ttgaggact atgggtgtct     60 atctctgaag taagatgacg tgtcagaaat tctatgtggt tttgttacac tgggaatttc    120
tgtatgtgat aactgcactt aacctggcct atccaacctc tccctggaga tttaagctgt    180
tttgtgcgcc accgagtaca actgatgact ccttcttctc tcctgctgga gtcccaaaca    240
atacttcgtc tttgaagggg gcttctgaag cacttgttga agctaaattt aattcaactg    300
gtatctacgt ttctgagtta tccaaaacca ttttccactg ttgctttggg aatgagcaag    360
gtcaaaactg ctccgcactc acaggcaaca ctgaagggaa gacgctggct tcagtggtga    420 agccttagt tttccgccaa ctaggtgtaa actgggacat agagtgctgg atgaaagggg    480
acttgacatt attcatctgt catatggaac cattacttaa gaacccctcc aagaattatg    540
actctaaggt tcaccttta tatgatctgc ctgaagttat agatgatttg cctctgcccc    600
cactgaaaga cagctttcag actgtccagt gcaactgcag tgttcgggaa tgcgaatgtc    660
atgtaccagt acccagagcc aaagtcaact acgctcttct gatgtattta gaaatcacat    720
ctgctggtgt gagtttttcag tcacctctaa tgtcactgca gcccatgctt gttgtgaagc    780
ccgatccacc gctgggtttg cgtatggaag tcacagatga tggtaattta agatttcat    840 gggacagcca aacaaaagca ccatttccac ttcaatatca ggtgaaatat ttagagaatt    900
ctacaatcgt aagagaggct gctgaaatcg tctcggatac atctctgctg gtagacagcg    960
tgcttcctgg gtcttcatac gaggtccagg tgaggagcaa gagactggat ggctcaggag    1020
tctggagtga ctggagttta cctcaactct ttaccacaca agatgtcatg tattttccac    1080
ccaaaattct gacgagtgtt ggatccaatg cttcctttg ctgcatctac aaaaatgaga    1140
accagactat ctcctcaaaa caatagtttt ggtggatgaa tctagccgag aagatccccg    1200
```

```
agacacagta caacactgtg agtgaccaca ttagcaaagt cactttctcc aacctgaaa     1260
ccaccagacc tcgagggaag tttacctatg atgcagtgta ctgctgcaat gagcaggct    1320
gccatcaccg ctacgctgaa ttatatgtga tcgatgtcaa tatcaatata tcatgtgaa    1380
ctgacgggta cttaactaaa atgacttgca gatggtcacc cagcacaatc caatcatag    1440
tgggaagcac tgtgcagttg aggtatcaca ggcgcagcct gtactgtccc gataaccat    1500
ctattcgtcc tacatcagag ctcaaaaact gcgtcttaca gacagatggc tttttgaat    1560
gtgttttcca gccaatcttt ctattatctg gctatacaat gtggatcagg atcaccatt    1620
ctttaggttc acttgactct ccaccaacgt gtgtccttcc tgactccgta gtaaaccac    1680
tacctccatc taatgtaaaa gcagagatta ctataaacac tggattattg aagtatctt    1740
gggaaaagcc agtctttcca gagaataacc ttcagttcca gattcgatat gcttaaatg    1800
gaaagaaat acaatggaag acacacgagg tattcgatgc aaaatcaaaatcggccagcc    1860
tgccagtgtc agatctctgt gcggtctatg tggtacaggt tcgctgccg cggttggatg    1920
gactagggta ttggagtaat tggagcagtc cagcctacac tcttgtcag gatgtaaaag    1980
ttcctatgag agggcctgaa ttctggagaa taatggatgg gatattct aaaaggaga     2040
gaaatgtcac cttgctttgg aagccactga tgaaaaatga ctcacttgt agtgtgagga    2100
ggtatgtggt gaagcatcgt actgcccaca atgggacatg gtcacagat gtgggaaatc    2160
agaccaatct cactttcctg tgggcagaat cagcacacac tgttcagtt ctggccatca    2220
attccatcgg tgcctccctt gtgaattta accttacgtt ctctggccc atgagtaaag    2280
tgaatgctgt gcagtcactc agtgcttatc ccctgagcag cactgcgtc atcctttcct    2340
ggacactgtc acctaatgat tatagtctgt tatatctggt tttgaatgg aagaaccta    2400
atgatgatga tggaatgaag tggcttagaa tcccttcgaa gttaacaag tattatatcc    2460
atgataattt tattcctatc gagaaatatc agtttagtctttacccagta tttatggaag    2520
gagttggaaa accaaagata attaatggtt tcaccaaag tgatatcgcc aaacagcaaa    2580
atgatgcagg gctgtatgtc attgtaccga taattattc ctcttgtgtc ctgctgctcg    2640
gaacactgtt aatttcacac cagagaatga aaaagtttt tgggacgat gttccaaacc    2700
ccaagaattg ttcctgggca caaggactta atttccaaa gataatgcct ggcagaaatt    2760
agaggatata gagtggatgc cgtcaaatgc ctttaactc tggcttccct ggctgtctca    2820
catctcccct attggagcta agtgtggtgc tgtattagc agggtatctg gcagatattt    2880
taaattaatt gaaatatcac cctaaatttc cagttctgg taaactgaag tgaatttcag    2940
aaattattgt atttatgtgt gtgcacatat gttgcaggt acccaccgaa atctgcagag    3000
gcatcagatg ccccagagct ggaactgaca gtgtgagcc tgatatgagt tctgggaatg    3060
agctcagtcc tctggaagag ctgcaagcac attaactgc tgagccatct tttcagtccc    3120
tcatgtatag attaaaaaaa attggggtttgaagatcctc atttgtgaga aattccttct    3180
tacctttgca aacactttt ctcatttt gtatatgtat tcatatttta ctgtctcatt    3240
ttcaatatat gtggtcacag ttttttaaga tttctaaggc ataacaaaga tgtaatatta    3300
agaataaata aaagaataaa tcaataacc agatggtagt gacagacacc tttaatccca    3360
gtactaagga gacagagata ggtaaactg tatgaatttg agacacgcct gttctacaaa    3420
gaaatttcag gacatctagg ggtatcaca agaaacact gtctcaaaaa atgccaaaca    3480
atcaaaaaaa aaaaa                                                    3495
```

<210> SEQ ID NO 18
<211> LENGTH: 389
<212> TYPE: DNA
<213> ORGANISM: Rattus Norvegicus

<400> SEQUENCE: 18

```
gtcactttt  aagtatttac  ccaagatatc  taaggttgca  gtttagatac  tctattacat      60
agagatcttt  aaacatcttt  aaaaggcttt  attttgtcct  gttcacttta  ttaatcccgt     120
ttatcctttg  tctatagcaa  tagctgggtt  ttggatttga  tcagaggaaa  caaagttcag     180
tcatttatca  catgagagtt  gacaaggtgt  cttttttttt  tctcgtcact  gtacataaaa     240
aaataaatac  tacaagagga  aggaacattg  tagatggaga  atagataact  gactaaaagg     300
gctttcttta  gtcaaaaagt  ttaggatcaa  tattatgagt  ttctgatatt  caatatttca     360
ccatgactta  caagtacagt  gttgttttt                                          389
```

<210> SEQ ID NO 19
<211> LENGTH: 895
<212> TYPE: PRT
<213> ORGANISM: Rattus Norvegicus

<400> SEQUENCE: 19

```
Met Thr Cys Gln Lys Phe Tyr Val Val Leu Leu His Trp Glu Phe Leu
 1               5                  10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
        35                  40                  45

Ser Pro Ala Gly Val Pro Asn Asn Thr Ser Ser Leu Lys Gly Ala Ser
    50                  55                  60

Glu Ala Leu Val Glu Ala Lys Phe Asn Ser Thr Gly Ile Tyr Val Ser
 65                 70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
            100                 105                 110

Ser Val Val Lys Pro Leu Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Leu Lys Asn Pro Phe Lys Asn Tyr Asp Ser Lys Val His
145                 150                 155                 160

Leu Leu Tyr Asp Leu Pro Glu Val Ile Asp Leu Pro Leu Pro Pro
                165                 170                 175

Leu Lys Asp Ser Phe Gln Thr Val Gln Cys Asn Cys Ser Val Arg Glu
            180                 185                 190

Cys Glu Cys His Val Pro Val Pro Arg Ala Lys Val Asn Tyr Ala Leu
        195                 200                 205

Leu Met Tyr Leu Glu Ile Thr Ser Ala Gly Val Ser Phe Gln Ser Pro
    210                 215                 220

Leu Met Ser Leu Gln Pro Met Leu Val Val Lys Pro Asp Pro Pro Leu
225                 230                 235                 240

Gly Leu Arg Met Glu Val Thr Asp Asp Gly Asn Leu Lys Ile Ser Trp
                245                 250                 255
```

-continued

```
Asp Ser Gln Thr Lys Ala Pro Phe Pro Leu Gln Tyr Gln Val Lys Tyr
            260                 265                 270
Leu Glu Asn Ser Thr Ile Val Arg Glu Ala Ala Glu Ile Val Ser Asp
            275                 280                 285
Thr Ser Leu Leu Val Asn Ser Val Leu Pro Gly Ser Ser Tyr Glu Val
            290                 295                 300
Gln Val Arg Ser Lys Arg Leu Asp Gly Ser Gly Val Trp Ser Asp Trp
305                 310                 315                 320
Ser Leu Pro Gln Leu Phe Thr Thr Gln Asp Val Met Tyr Phe Pro Pro
                325                 330                 335
Lys Ile Leu Thr Ser Val Gly Ser Asn Ala Ser Phe Cys Cys Ile Tyr
                340                 345                 350
Lys Asn Glu Asn Gln Thr Ile Ser Ser Lys Gln Ile Val Trp Trp Met
            355                 360                 365
Asn Leu Ala Glu Lys Ile Pro Glu Thr Gln Tyr Asn Thr Val Ser Asp
            370                 375                 380
His Ile Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
                420                 425                 430
Ser Cys Glu Thr Asp Gly Tyr Leu Thr Lys Met Thr Cys Arg Trp Ser
            435                 440                 445
Pro Ser Thr Ile Gln Ser Leu Val Gly Ser Thr Val Gln Leu Lys Tyr
            450                 455                 460
His Arg Arg Ser Leu Tyr Cys Pro Asp Asn Pro Ser Ile Arg Pro Thr
465                 470                 475                 480
Ser Glu Leu Lys Asn Cys Val Leu Gln Thr Asp Gly Phe Tyr Glu Cys
                485                 490                 495
Val Phe Gln Pro Ile Phe Leu Leu Ser Gly Tyr Thr Met Trp Ile Arg
                500                 505                 510
Ile Asn His Ser Leu Gly Ser Leu Asp Ser Pro Pro Thr Cys Val Leu
            515                 520                 525
Pro Asp Ser Val Val Lys Pro Leu Pro Pro Ser Asn Val Lys Ala Glu
            530                 535                 540
Ile Thr Ile Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Asn Gly
                565                 570                 575
Lys Glu Ile Gln Trp Lys Thr His Glu Val Phe Asp Ala Lys Ser Lys
                580                 585                 590
Ser Ala Ser Leu Pro Val Ser Asp Leu Cys Ala Val Tyr Val Val Gln
            595                 600                 605
Val Arg Cys Arg Arg Leu Asp Gly Leu Gly Tyr Trp Ser Asn Trp Ser
            610                 615                 620
Ser Pro Ala Tyr Thr Leu Val Met Asp Val Lys Val Pro Met Arg Gly
625                 630                 635                 640
Pro Glu Phe Trp Arg Ile Met Asp Gly Asp Ile Thr Lys Lys Glu Arg
                645                 650                 655
Asn Val Thr Leu Leu Trp Lys Pro Leu Met Lys Asn Asp Ser Leu Cys
            660                 665                 670
```

```
Ser Val Arg Arg Tyr Val Val Lys His Arg Thr Ala His Asn Gly Thr
            675                 680                 685

Trp Ser Gln Asp Val Gly Asn Gln Thr Asn Leu Thr Phe Leu Trp Ala
    690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
                725                 730                 735

Asn Ala Val Gln Ser Leu Ser Ala Tyr Pro Leu Ser Ser Ser Cys Val
            740                 745                 750

Ile Leu Ser Trp Thr Leu Ser Pro Asn Asp Tyr Ser Leu Leu Tyr Leu
        755                 760                 765

Val Ile Glu Trp Lys Asn Leu Asn Asp Asp Asp Gly Met Lys Trp Leu
    770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Asp Ile Ala
            820                 825                 830

Lys Gln Gln Asn Asp Ala Gly Leu Tyr Val Ile Val Pro Ile Ile Ile
        835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Ile Met Pro Gly Arg Asn
                885                 890                 895

<210> SEQ ID NO 20
<211> LENGTH: 1162
<212> TYPE: PRT
<213> ORGANISM: Rattus Norvegicus

<400> SEQUENCE: 20

Met Thr Cys Gln Lys Phe Tyr Val Val Leu Leu His Trp Glu Phe Leu
1               5                   10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
        35                  40                  45

Ser Pro Ala Gly Val Pro Asn Asn Thr Ser Ser Leu Lys Gly Ala Ser
    50                  55                  60

Glu Ala Leu Val Glu Ala Lys Phe Asn Ser Thr Gly Ile Tyr Val Ser
65                  70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
            100                 105                 110

Ser Val Val Lys Pro Leu Val Phe Arg Gln Leu Gly Val Asn Trp Asp
        115                 120                 125

Ile Glu Cys Trp Met Lys Gly Asp Leu Thr Leu Phe Ile Cys His Met
    130                 135                 140

Glu Pro Leu Leu Lys Asn Pro Phe Lys Asn Tyr Asp Ser Lys Val His
145                 150                 155                 160
```

```
Leu Leu Tyr Asp Leu Pro Glu Val Ile Asp Asp Leu Pro Leu Pro Pro
                165                 170                 175
Leu Lys Asp Ser Phe Gln Thr Val Gln Cys Asn Cys Ser Val Arg Glu
                180                 185                 190
Cys Glu Cys His Val Pro Val Pro Arg Ala Lys Val Asn Tyr Ala Leu
                195                 200                 205
Leu Met Tyr Leu Glu Ile Thr Ser Ala Gly Val Ser Phe Gln Ser Pro
                210                 215                 220
Leu Met Ser Leu Gln Pro Met Leu Val Val Lys Pro Asp Pro Pro Leu
225                 230                 235                 240
Gly Leu Arg Met Glu Val Thr Asp Asp Gly Asn Leu Lys Ile Ser Trp
                245                 250                 255
Asp Ser Gln Thr Lys Ala Pro Phe Pro Leu Gln Tyr Pro Val Lys Tyr
                260                 265                 270
Leu Glu Asn Ser Thr Ile Val Arg Glu Ala Ala Glu Ile Val Ser Asp
                275                 280                 285
Thr Ser Leu Leu Val Asn Ser Val Leu Pro Gly Ser Ser Tyr Glu Val
                290                 295                 300
Gln Val Arg Ser Lys Arg Leu Asp Gly Ser Gly Val Trp Ser Asp Trp
305                 310                 315                 320
Ser Leu Pro Gln Leu Phe Thr Thr Gln Asp Val Met Tyr Phe Pro Pro
                325                 330                 335
Lys Ile Leu Thr Ser Val Gly Ser Asn Ala Ser Phe Cys Cys Ile Tyr
                340                 345                 350
Lys Asn Glu Asn Gln Thr Ile Ser Ser Lys Gln Ile Val Trp Trp Met
                355                 360                 365
Asn Leu Ala Glu Lys Ile Pro Glu Thr Gln Tyr Asn Thr Val Ser Asp
                370                 375                 380
His Ile Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
                405                 410                 415
His His Arg Tyr Ala Glu Leu Tyr Val Ile Asp Val Asn Ile Asn Ile
                420                 425                 430
Ser Cys Glu Thr Asp Gly Tyr Leu Thr Lys Met Thr Cys Arg Trp Ser
                435                 440                 445
Pro Ser Thr Ile Gln Ser Leu Val Gly Ser Thr Val Gln Leu Lys Tyr
                450                 455                 460
His Arg Arg Ser Leu Tyr Cys Pro Asp Asn Pro Ser Ile Arg Pro Thr
465                 470                 475                 480
Ser Glu Leu Lys Asn Cys Val Leu Gln Thr Asp Gly Phe Tyr Glu Cys
                485                 490                 495
Val Phe Gln Pro Ile Phe Leu Leu Ser Gly Tyr Thr Met Trp Ile Arg
                500                 505                 510
Ile Asn His Ser Leu Gly Ser Leu Asp Ser Pro Pro Thr Cys Val Leu
                515                 520                 525
Pro Asp Ser Val Val Lys Pro Leu Pro Pro Ser Asn Val Lys Ala Glu
530                 535                 540
Ile Thr Ile Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Asn Gly
                565                 570                 575
```

-continued

```
Lys Glu Ile Gln Trp Lys Thr His Glu Val Phe Asp Ala Lys Ser Lys
            580                 585                 590

Ser Ala Ser Leu Pro Val Ser Asp Leu Cys Ala Val Tyr Val Val Gln
            595                 600                 605

Val Arg Cys Arg Arg Leu Asp Gly Leu Gly Tyr Trp Ser Asn Trp Ser
            610                 615                 620

Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
            645                 650                 655

Asn Val Thr Leu Leu Trp Lys Pro Leu Met Lys Asn Asp Ser Leu Cys
            660                 665                 670

Ser Val Arg Arg Tyr Val Val Lys His Arg Thr Ala His Asn Gly Thr
            675                 680                 685

Trp Ser Gln Asp Val Gly Asn Gln Thr Asn Leu Thr Phe Leu Trp Ala
            690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
            725                 730                 735

Asn Ala Val Gln Ser Leu Ser Ala Tyr Pro Leu Ser Ser Ser Cys Val
            740                 745                 750

Ile Leu Ser Trp Thr Leu Ser Pro Asn Asp Tyr Ser Leu Leu Tyr Leu
            755                 760                 765

Val Ile Glu Trp Lys Asn Leu Asn Asp Asp Gly Met Lys Trp Leu
770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
            805                 810                 815

Val Gly Lys Pro Lys Ile Ile Asn Gly Phe Thr Lys Asp Asp Ile Ala
            820                 825                 830

Lys Gln Gln Asn Asp Ala Gly Leu Tyr Val Ile Val Pro Ile Ile Ile
            835                 840                 845

Ser Ser Cys Val Leu Leu Leu Gly Thr Leu Leu Ile Ser His Gln Arg
            850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
            885                 890                 895

Phe Thr Lys His Ala Glu Ser Val Ile Phe Gly Pro Leu Leu Leu Glu
            900                 905                 910

Pro Glu Pro Val Ser Glu Glu Ile Ser Val Asp Thr Ala Trp Lys Asn
            915                 920                 925

Lys Asp Glu Met Val Pro Ala Ala Met Val Ser Leu Leu Leu Thr Thr
            930                 935                 940

Pro Asp Ser Thr Arg Gly Ser Ile Cys Ile Ser Asp Gln Cys Asn Ser
945                 950                 955                 960

Ala Asn Phe Ser Gly Ala Gln Ser Thr Gln Gly Thr Cys Glu Asp Glu
            965                 970                 975

Cys Gln Ser Gln Pro Ser Val Lys Tyr Ala Thr Leu Val Ser Asn Val
            980                 985                 990
```

```
Lys Thr Val Glu Thr Asp Glu Glu Gln Gly Ala Ile His Ser Ser Val
        995                 1000                1005

Ser Gln Cys Ile Ala Arg Lys His Ser Pro Leu Arg Gln Ser Phe Ser
    1010                1015                1020

Ser Asn Ser Trp Glu Ile Glu Ala Gln Ala Phe Phe Leu Leu Ser Asp
1025                1030                1035                1040

His Pro Pro Asn Val Ile Ser Pro Gln Leu Ser Phe Ser Gly Leu Asp
                1045                1050                1055

Glu Leu Leu Glu Leu Glu Gly Asn Phe Pro Glu Glu Asn His Gly Glu
            1060                1065                1070

Lys Ser Val Tyr Tyr Leu Gly Val Ser Ser Gly Asn Lys Arg Glu Asn
            1075                1080                1085

Asp Met Leu Leu Thr Asp Glu Ala Gly Val Leu Cys Pro Phe Pro Ala
    1090                1095                1100

His Cys Leu Phe Ser Asp Ile Arg Ile Leu Gln Glu Ser Cys Ser His
1105                1110                1115                1120

Phe Val Glu Asn Asn Leu Asn Leu Gly Thr Ser Gly Lys Asn Phe Val
                1125                1130                1135

Pro Tyr Met Pro Gln Phe Gln Ser Cys Ser Thr His Ser His Lys Ile
            1140                1145                1150

Ile Glu Asn Lys Met Cys Asp Leu Thr Val
            1155                1160

<210> SEQ ID NO 21
<211> LENGTH: 895
<212> TYPE: PRT
<213> ORGANISM: Rattus Norvegicus

<400> SEQUENCE: 21

Met Thr Cys Gln Lys Phe Tyr Val Val Leu Leu His Trp Glu Phe Leu
1               5                   10                  15

Tyr Val Ile Thr Ala Leu Asn Leu Ala Tyr Pro Thr Ser Pro Trp Arg
            20                  25                  30

Phe Lys Leu Phe Cys Ala Pro Pro Ser Thr Thr Asp Asp Ser Phe Leu
        35                  40                  45

Ser Pro Ala Gly Val Pro Asn Asn Thr Ser Ser Leu Lys Gly Ala Ser
50                  55                  60

Glu Ala Leu Val Glu Ala Lys Phe Asn Ser Thr Gly Ile Tyr Val Ser
65                  70                  75                  80

Glu Leu Ser Lys Thr Ile Phe His Cys Cys Phe Gly Asn Glu Gln Gly
                85                  90                  95

Gln Asn Cys Ser Ala Leu Thr Gly Asn Thr Glu Gly Lys Thr Leu Ala
            100                 105                 110

Ser Val Val Lys Pro Leu Val Phe Arg Gln Leu Gly Val Asn Trp Asp
        115                 120                 125

Ile Glu Cys Trp Met Lys Gly Asp Leu Thr Leu Phe Ile Cys His Met
130                 135                 140

Glu Pro Leu Leu Lys Asn Pro Phe Lys Asn Tyr Asp Ser Lys Val His
145                 150                 155                 160

Leu Leu Tyr Asp Leu Pro Glu Val Ile Asp Asp Leu Pro Leu Pro Pro
                165                 170                 175

Leu Lys Asp Ser Phe Gln Thr Val Gln Cys Asn Cys Ser Val Arg Glu
            180                 185                 190

Cys Glu Cys His Val Pro Val Pro Arg Ala Lys Val Asn Tyr Ala Leu
        195                 200                 205
```

-continued

```
Leu Met Tyr Leu Glu Ile Thr Ser Ala Gly Val Ser Phe Gln Ser Pro
    210                 215                 220
Leu Met Ser Leu Gln Pro Met Leu Val Val Lys Pro Asp Pro Pro Leu
225                 230                 235                 240
Gly Leu Arg Met Glu Val Thr Asp Asp Gly Asn Leu Lys Ile Ser Trp
            245                 250                 255
Asp Ser Gln Thr Lys Ala Pro Phe Pro Leu Gln Tyr Pro Ile Met Pro
                260                 265                 270
Gly Arg Asn Ser Thr Ile Val Arg Glu Ala Ala Glu Ile Val Ser Asp
            275                 280                 285
Thr Ser Leu Leu Val Asn Ser Val Leu Pro Gly Ser Ser Tyr Glu Val
            290                 295                 300
Gln Val Arg Ser Lys Arg Leu Asp Gly Ser Gly Val Trp Ser Asp Trp
305                 310                 315                 320
Ser Leu Pro Gln Leu Phe Thr Thr Gln Asp Val Met Tyr Phe Pro Pro
                325                 330                 335
Lys Ile Leu Thr Ser Val Gly Ser Asn Ala Ser Phe Cys Cys Ile Tyr
            340                 345                 350
Lys Asn Glu Asn Gln Thr Ile Ser Ser Lys Gln Ile Val Trp Trp Met
            355                 360                 365
Asn Leu Ala Glu Lys Ile Pro Glu Thr Gln Tyr Asn Thr Val Ser Asp
            370                 375                 380
His Ile Ser Lys Val Thr Phe Ser Asn Leu Lys Ala Thr Arg Pro Arg
385                 390                 395                 400
Gly Lys Phe Thr Tyr Asp Ala Val Tyr Cys Cys Asn Glu Gln Ala Cys
            405                 410                 415
His His Arg Tyr Ala Glu Leu Tyr Val Ile Asp Val Asn Ile Asn Ile
            420                 425                 430
Ser Cys Glu Thr Asp Gly Tyr Leu Thr Lys Met Thr Cys Arg Trp Ser
        435                 440                 445
Pro Ser Thr Ile Gln Ser Leu Val Gly Ser Thr Val Gln Leu Lys Tyr
        450                 455                 460
His Arg Arg Ser Leu Tyr Cys Pro Asp Asn Pro Ser Ile Arg Pro Thr
465                 470                 475                 480
Ser Glu Leu Lys Asn Cys Val Leu Gln Thr Asp Gly Phe Tyr Glu Cys
            485                 490                 495
Val Phe Gln Pro Ile Phe Leu Leu Ser Gly Tyr Thr Met Trp Ile Arg
        500                 505                 510
Ile Asn His Ser Leu Gly Ser Leu Asp Ser Pro Pro Thr Cys Val Leu
        515                 520                 525
Pro Asp Ser Val Val Lys Pro Leu Pro Pro Ser Asn Val Lys Ala Glu
530                 535                 540
Ile Thr Ile Asn Thr Gly Leu Leu Lys Val Ser Trp Glu Lys Pro Val
545                 550                 555                 560
Phe Pro Glu Asn Asn Leu Gln Phe Gln Ile Arg Tyr Gly Leu Asn Gly
            565                 570                 575
Lys Glu Ile Gln Trp Lys Thr His Glu Val Phe Asp Ala Lys Ser Lys
            580                 585                 590
Ser Ala Ser Leu Pro Val Ser Asp Leu Cys Ala Val Tyr Val Val Gln
        595                 600                 605
Val Arg Cys Arg Arg Leu Asp Gly Leu Gly Tyr Trp Ser Asn Trp Ser
610                 615                 620
```

```
Ser Pro Ala Tyr Thr Leu Val Met Asp Val Lys Val Pro Met Arg Gly
625                 630                 635                 640

Pro Glu Phe Trp Arg Ile Met Asp Gly Asp Ile Thr Lys Lys Glu Arg
                645                 650                 655

Asn Val Thr Leu Leu Trp Lys Pro Leu Met Lys Asn Asp Ser Leu Cys
                660                 665                 670

Ser Val Arg Arg Tyr Val Val Lys His Arg Thr Ala His Asn Gly Thr
                675                 680                 685

Trp Ser Gln Asp Val Gly Asn Gln Thr Asn Leu Thr Phe Leu Trp Ala
                690                 695                 700

Glu Ser Ala His Thr Val Thr Val Leu Ala Ile Asn Ser Ile Gly Ala
705                 710                 715                 720

Ser Leu Val Asn Phe Asn Leu Thr Phe Ser Trp Pro Met Ser Lys Val
                725                 730                 735

Asn Ala Val Gln Ser Leu Ser Ala Tyr Pro Leu Ser Ser Ser Cys Val
                740                 745                 750

Ile Leu Ser Trp Thr Leu Ser Pro Asn Asp Tyr Ser Leu Leu Tyr Leu
                755                 760                 765

Val Ile Glu Trp Lys Asn Leu Asn Asp Asp Asp Gly Met Lys Trp Leu
770                 775                 780

Arg Ile Pro Ser Asn Val Asn Lys Tyr Tyr Ile His Asp Asn Phe Ile
785                 790                 795                 800

Pro Ile Glu Lys Tyr Gln Phe Ser Leu Tyr Pro Val Phe Met Glu Gly
                805                 810                 815

Val Gly Lys Pro Lys Ile Ile Asn Gly Phe Thr Lys Asp Asp Ile Ala
                820                 825                 830

Lys Gln Gln Asn Asp Ala Gly Leu Tyr Val Ile Val Pro Ile Ile Ile
                835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Ile Met Pro Gly Arg Asn
                885                 890                 895
```